United States Patent
Sakai

(10) Patent No.: US 7,873,501 B2
(45) Date of Patent: Jan. 18, 2011

(54) CRACK GROWTH EVALUATION APPARATUS, CRACK GROWTH EVALUATION METHOD, AND RECORDING MEDIUM RECORDING CRACK GROWTH EVALUATION PROGRAM

(75) Inventor: Hidehisa Sakai, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 575 days.

(21) Appl. No.: 11/984,310

(22) Filed: Nov. 15, 2007

(65) Prior Publication Data
US 2008/0172211 A1 Jul. 17, 2008

(30) Foreign Application Priority Data
Jan. 11, 2007 (JP) ............... 2007-002965

(51) Int. Cl.
G06F 9/455 (2006.01)
(52) U.S. Cl. .......................................... 703/7
(58) Field of Classification Search ..................... 703/1, 703/7, 2, 22, 6; 702/34, 35, 36, 183; 623/1.15; 310/338; 73/587, 865.8
See application file for complete search history.

(56) References Cited

U.S. PATENT DOCUMENTS

| | | | | |
|---|---|---|---|---|
| 5,455,777 | A * | 10/1995 | Fujiyama et al. | 702/34 |
| 5,826,213 | A * | 10/1998 | Kennefick | 702/35 |
| 6,006,163 | A * | 12/1999 | Lichtenwalner et al. | 702/36 |
| 7,480,601 | B2 * | 1/2009 | Tryon, III | 703/7 |
| 2001/0047691 | A1 * | 12/2001 | Dzenis | 73/587 |
| 2004/0031337 | A1 * | 2/2004 | Masaniello et al. | 73/865.8 |
| 2004/0148143 | A1 * | 7/2004 | Deobald et al. | 703/2 |
| 2004/0158450 | A1 * | 8/2004 | Nakadate et al. | 703/22 |
| 2004/0225474 | A1 * | 11/2004 | Goldfine et al. | 702/183 |
| 2005/0200243 | A1 * | 9/2005 | Spangler et al. | 310/338 |
| 2006/0009837 | A1 * | 1/2006 | Burgermeister et al. | 623/1.15 |
| 2006/0089823 | A1 * | 4/2006 | Meyer et al. | 703/2 |

(Continued)

FOREIGN PATENT DOCUMENTS

JP 2004-045343 2/2004

(Continued)

OTHER PUBLICATIONS

Simonovski et al., "The influence of crystallographic orientation on crack tip displacements of microstructurally small, kinked crack crossing the grain boundary", Computational Materials Science, 2006.*

(Continued)

*Primary Examiner*—Paul L Rodriguez
*Assistant Examiner*—Kandasamy Thangavelu
(74) *Attorney, Agent, or Firm*—Staas & Halsey LLP

(57) ABSTRACT

The analysis model generation unit generates an analysis model for use in an analysis by a finite-element method. A stress distortion analysis unit analyzes a stress and a distortion occurring in finite elements of a continuum by a load using the analysis model for each load cycle cyclically applied to the continuum by the finite-element method. An element damage evaluation unit evaluates a damage by the distortion on the finite elements of the continuum based on the analysis result for each load cycle. A crack growth display unit displays the growth of a crack occurring in the continuum based on a result of the evaluation of the damage.

14 Claims, 14 Drawing Sheets

U.S. PATENT DOCUMENTS

2006/0206295 A1\* 9/2006 Tryon, III ..................... 703/6

FOREIGN PATENT DOCUMENTS

JP          2006-071406        3/2006

OTHER PUBLICATIONS

Harte et al., "On progressive damage phenomena of structures", Computational Mechanics, 2000.\*

Mohr, W, "Strain based design of pipelines", U.S. Department of Interior, Minerals and management Service, 2003.\*

\* cited by examiner

US 7,873,501 B2

CRACK GROWTH EVALUATION APPARATUS, CRACK GROWTH EVALUATION METHOD, AND RECORDING MEDIUM RECORDING CRACK GROWTH EVALUATION PROGRAM

CROSS-REFERENCE TO RELATED APPLICATIONS

This application claims the conventional priority based on Japanese Application No. 2007-002965, filed on Jan. 11, 2007, the disclosures of which are incorporated herein by reference.

BACKGROUND OF THE INVENTION

1. Field of the Invention

The present invention relates to a crack growth evaluation apparatus, a crack growth evaluation method, and a recording medium recording a crack growth evaluation program, and particularly to a crack growth evaluation apparatus, a crack growth evaluation method, and a recording medium recording a crack growth evaluation program for evaluating the growth of a crack occurring in a continuum using a finite-element method.

2. Description of the Related Art

For a solder material and various types of joining resin material (adhesive), stable connection reliability of a junction is important. Specifically, it is necessary for a connected portion to have a sufficient durability in the temperature cycle and mechanical cycle such as vibration and so on cyclically applied in a practical use environment. At a designing stage for a connected portion, there is a method for calculating a stress and a distortion simulated using the finite-element method and so on, and indirectly evaluating a life and so on based on a value of a calculated stress and a distortion. This method has been widely used in evaluating many parts and the development of a device. Especially, in estimating the count of the cyclic fatigue life such as a temperature cycle fatigue, a method of estimating the cyclic fatigue life count using the Manson-Coffin law based on a distortion value obtained from the simulation result using the finite-element method and so on.

FIG. 15 shows an analysis model of a soldered junction 102. The analysis model is used for a simulation in the finite-element method and so on. There has been the conventional method for calculating a cyclic fatigue life count $N_f$ by the Manson-Coffin law expressed in the following equation 1 after obtaining a distortion amplitude value $\Delta\epsilon_{in}$ using the analysis model for the finite element of the portion enclosed by the bold circle.

$$N_f = 1/2 \cdot (\Delta\epsilon_{in}/\epsilon_o)^{-n} \quad \text{(equation 1)}$$

In the equation 1 above, n and $\epsilon_o$ are constants.

For the structure of the electrode of an electronic component, a life check apparatus for calculating the fracture life of a soldered portion has been proposed (refer to Japanese Patent Laid-Open No. 2004-45343).

The conventional technique of calculating the cyclic fatigue life count $N_f$ based on the finite-element method and the Manson-Coffin law (hereinafter referred to simply as conventional technique) is the technique to evaluate the life using a stress and a distortion occurring in the soldered portion having an initial geometry. Therefore, the cyclic fatigue life count can be estimated with high accuracy when there occurs a crack in the soldered portion.

However, since the initial geometry (geometry at production) is used as the geometry of an analysis model of a soldered portion in the conventional technique, it is hard to estimate a stress status when a crack grows in the soldered portion. The tests of a temperature cycle and a mechanical cycle are performed in several hundred cycles to several tens of thousand cycles, but the current computers require several hours to several days to perform the calculation per cycle. Therefore, it is not practical to perform several hundred of cycles on a computer because it takes too much calculation time. Therefore, in the conventional technique, it is substantially hard to estimate a complete fracture life to the final fracture or the growth of a crack when a crack grows in the soldered portion.

SUMMARY OF THE INVENTION

It is an object of the present invention to provide a crack growth evaluation apparatus that evaluates the growth of a crack from the generation of the initial crack in a continuum to the final fracture of the crack.

It is another object of the present invention provide a crack growth evaluation method for evaluating the growth of a crack from the generation of the initial crack in a continuum to the final fracture of the crack.

It is still another object of the present invention to provide a recording medium recording a crack growth evaluation program for evaluating the growth of a crack from the generation of the initial crack in a continuum to the final fracture of the crack.

The crack growth evaluation apparatus according to the present invention is the crack growth evaluation apparatus that evaluates growth of a crack occurring in a continuum. The crack growth evaluation apparatus comprises a model generation unit generating an analysis model used in analyzing a stress and a distortion occurring in the continuum by a finite-element method and obtained by dividing the continuum into a plurality of finite elements, an analysis unit analyzing by the finite-element method a stress and a distortion occurring by a load cyclically applied to the continuum in each of the plurality of finite elements of the continuum for each cycle of the load using the analysis model, an evaluation unit evaluating damage caused by the distortion occurring in the continuum for each of the plurality of finite elements of the continuum for each cycle of the load cyclically applied to the continuum using the analysis model based on a result of an analysis by the analysis unit, and a display unit displaying growth of a crack occurring in the continuum using the analysis model based on a result of an evaluation of the damage by the evaluation unit.

Preferably, the crack growth evaluation apparatus further comprises a change unit changing rigidity of each of the plurality of finite elements of the continuum based on the result of the evaluation of the damage using the analysis model. The analysis unit analyzes the stress and the distortion occurring by a load in a next cycle to the current cycle on each of the plurality of finite elements of the continuum whose rigidity is changed by the load of the current cycle of the cycles of the load.

Preferably, the evaluation unit calculates an cumulative nonlinear distortion value on each of the plurality of finite elements of the continuum, calculates a nonlinear distortion amplitude value based on the cumulative nonlinear distortion value, calculates a damage value using a Manson-Coffin law based on the nonlinear distortion amplitude value, calculates a cumulative value of the damage value based on the damage value, and compares the cumulative value with a predetermined threshold. The change unit changes the rigidity of a finite element on each of the plurality of finite elements of the continuum based on result of a comparison by the evaluation unit.

Preferably, the evaluation unit calculates the nonlinear distortion amplitude value in the current cycle by subtracting a cumulative nonlinear distortion value in a cycle immediately before the current cycle from a cumulative nonlinear distortion value in the current cycle of the cycles of the load for each of the plurality of finite elements of the continuum.

Preferably, the evaluation unit obtains an average value of the cumulative nonlinear distortion value based on the cumulative nonlinear distortion value in a cycle of the load in a predetermined order and a count up to the cycle of the load in the predetermined order for each of the plurality of finite elements of the continuum, and calculates the nonlinear distortion amplitude value in the cycle of the load in the predetermined order based on the average value.

Preferably, the evaluation unit calculates a damage value obtained when a load equal to the load in the current cycle of the cycles of the load is applied to the continuum by the number of times of a predetermined value for each of the plurality of finite elements of the continuum by multiplying the damage value in the current cycle by the predetermined value.

Preferably, the evaluation unit calculates a change rate of the damage value for each of the plurality of finite elements of the continuum, and calculates the damage value obtained when applying a load equal to the load in the current cycle of the cycles of the load to the continuum the number of times of a predetermined value corresponding to the change rate by multiplying the damage value in the current cycle by the predetermined value.

Preferably, the display unit displays growth of a crack occurring in the continuum for one or more predetermined load cycles.

The crack growth evaluation method according to the present invention is the crack growth evaluation method for evaluating growth of a crack occurring in a continuum. The crack growth evaluation method comprises generating an analysis model used in analyzing a stress and a distortion occurring in the continuum by a finite-element method and obtained by dividing the continuum into a plurality of finite elements, analyzing by the finite-element method a stress and a distortion occurring by a load cyclically applied to the continuum for each of the plurality of finite elements of the continuum in each cycle of the load using the analysis model, evaluating damage caused by the distortion occurring in the continuum for each of the plurality of finite elements of the continuum for each cycle of the load cyclically applied to the continuum using the analysis model based on a result of the analysis, and displaying the growth of a crack occurring in the continuum using the analysis model based on a result of the evaluation of the damage.

The computer readable recording medium recording a crack growth evaluation program according to the present invention is the computer readable recording medium recording a crack growth evaluation program for evaluating growth of a crack occurring in a continuum. The program causes a computer to execute generating an analysis model used in analyzing a stress and a distortion occurring in the continuum by a finite-element method and obtained by dividing the continuum into a plurality of finite elements, analyzing by the finite-element method a stress and a distortion occurring by a load cyclically applied to the continuum in each of the plurality of finite elements of the continuum for each cycle of the load using the analysis model, evaluating damage caused by the distortion occurring in the continuum for each of the plurality of finite elements of the continuum for each cycle of the load cyclically applied to the continuum using the analysis model based on a result of the analysis, and displaying the growth of a crack occurring in the continuum using the analysis model based on a result of the evaluation of the damage.

The crack growth evaluation apparatus and the crack growth evaluation method according to the present invention generate an analysis model of a continuum, evaluate the damage of each of a plurality of finite elements of the continuum based on a result of an analysis of a stress and a distortion using the analysis model, and display the growth of a crack occurring in the continuum based on a result of the evaluation of the damage. Thus, according to the present invention, by evaluating the damage of each finite element, the growth of the crack occurring in the continuum can be known in a process of relatively small amount of computation. Therefore, a required processing time can be shortened. Additionally, according to the present invention, using an analysis model of a continuum generated in an initial process, a crack growth evaluation process can be performed. Therefore, the present invention can evaluate the growth of the crack without regenerating the analysis model depending on the growth of the crack.

Furthermore, the crack growth evaluation apparatus according to the present invention further changes the rigidity of each of the plurality of finite elements of the continuum based on the result of the evaluation of the damage using the analysis model, and cyclically analyzes the stress and the distortion on each of the plurality of finite elements of the continuum whose rigidity has been changed. Thus, according to the present invention, the growth of the crack occurring in the continuum can be evaluated only by changing the rigidity of each of the finite elements of the continuum without changing the analysis model. Therefore, a required processing time can be shortened.

Additionally, the crack growth evaluation apparatus according to the present invention calculates an cumulative nonlinear distortion value on each of the plurality of finite elements of the continuum, calculates a nonlinear distortion amplitude value based on the cumulative nonlinear distortion value, calculates a damage value using a Manson-Coffin law based on the nonlinear distortion amplitude value, calculates a cumulative value of the damage value based on the damage value, compares the cumulative value with a predetermined threshold, and changes the rigidity of a finite element based on a result of the comparison. Thus, according to the present invention, the damage of each finite element can be relatively easily evaluated. As a result, the growth of a crack occurring in the continuum can be known in a process for relatively small amount of computation. Furthermore, the growth of the crack can be evaluated using an analysis model of the continuum generated in an initial process without regenerating the analysis model depending on the growth of the crack.

Additionally, the crack growth evaluation apparatus according to the present invention calculates the nonlinear distortion amplitude value in the current cycle by subtracting a cumulative nonlinear distortion value in a cycle immediately before the current cycle from a cumulative nonlinear distortion value in the current cycle. Thus, the nonlinear distortion amplitude value in the current cycle can be correctly and easily calculated.

The crack growth evaluation apparatus according to the present invention obtains an average value of the cumulative nonlinear distortion value based on the cumulative nonlinear distortion value and a count for each of the plurality of finite elements of the continuum, and calculates the nonlinear distortion amplitude value in the cycle based on the average value. Thus, the present invention can easily calculate nonlinear distortion amplitude value in the current cycle without calculating the nonlinear distortion amplitude value for each of the plurality of load cycles. Therefore, the calculating time of the nonlinear distortion amplitude value can be shortened.

The crack growth evaluation apparatus according to the present invention calculates a damage value obtained when a load equal to the load in the current cycle of the cycles of the load is applied to the continuum by the number of times of a predetermined value by multiplying the damage value in the current cycle by the predetermined value. Thus, the damage value (cumulative damage value) in the current cycle can be easily calculated without calculating the damage value in each of the plurality of load cycles, and the calculating time of the cumulative damage value can be shortened.

The crack growth evaluation apparatus according to the present invention calculates a change rate of the calculated damage value, and calculates the damage value (cumulative damage value) obtained by applying a load the number of times of a predetermined value corresponding to the change rate by multiplying the calculated damage value by the predetermined value. Thus, the cumulative damage value can be efficiently calculated with high accuracy by multiplying the damage value by the predetermined value without calculating a cumulative damage value for each load cycle.

The crack growth evaluation apparatus according to the present invention displays the growth of a crack for predetermined load cycles. Therefore, for example, a portion requiring the reinforcement by a design change in a continuum can be easily recognized, and the effect of the design change in the continuum can be easily recognized.

DETAILED DESCRIPTION OF THE PREFERRED EMBODIMENTS

Figure 1:
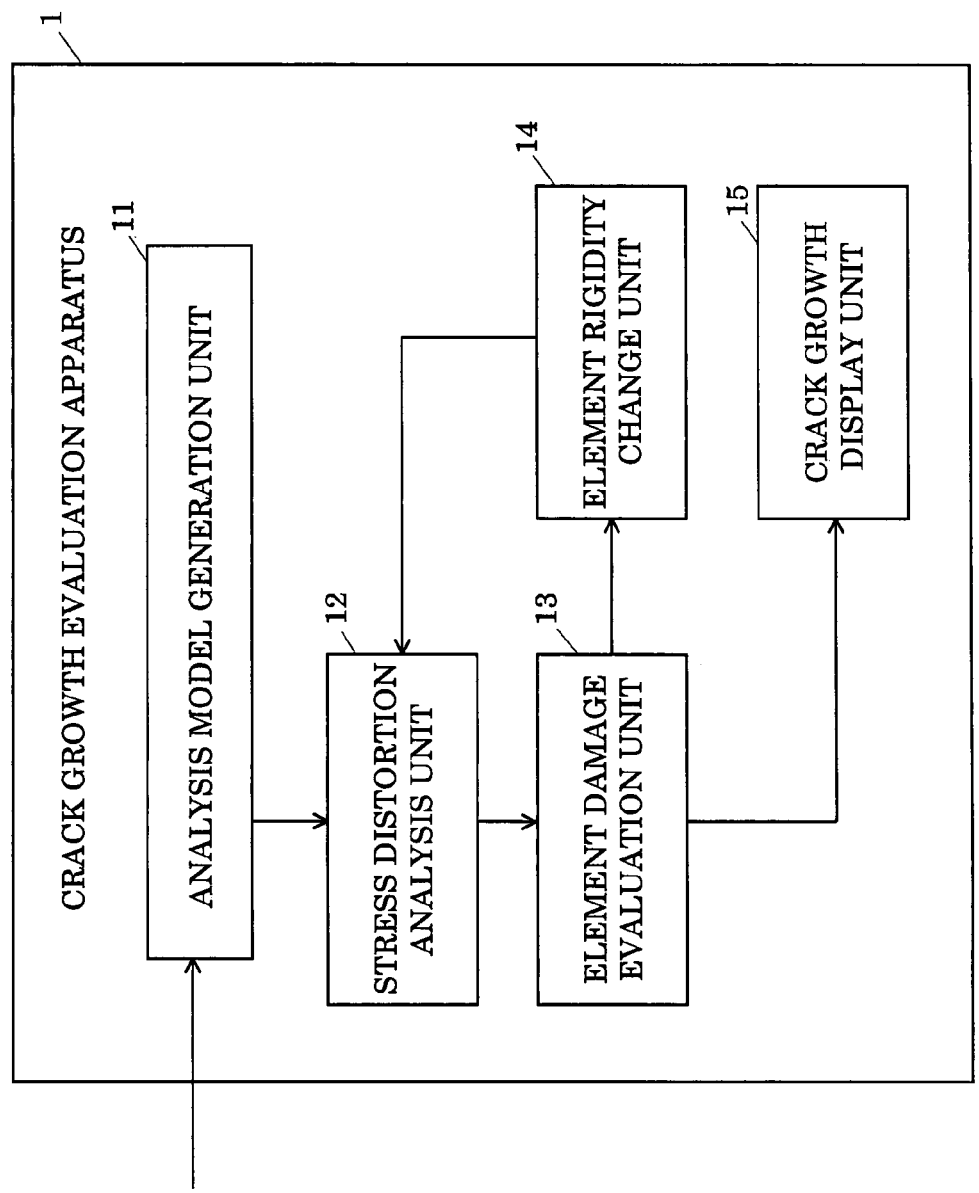
FIG. 1 shows an example of a structure of a crack growth evaluation apparatus according to the present invention.

FIG. 1 shows an example of a structure of a crack growth evaluation apparatus according to the present invention. A crack growth evaluation apparatus 1 is a computer that evaluates the growth of a crack occurring in a continuum. The crack growth evaluation apparatus 1 includes an analysis model generation unit 11, a stress distortion analysis unit 12, an element damage evaluation unit 13, an element rigidity change unit 14, and a crack growth display unit 15. Each of the units provided for the crack growth evaluation apparatus 1 is realized by a CPU and a program prepared on main memory and executed by the CPU.

The analysis model generation unit (hereinafter referred to as a generation unit) 11 generates an analysis model of a continuum as an object in evaluating the growth of a crack. The analysis model is a model (finite element model) used in an analysis (simulation) in a finite-element method for a stress and a distortion occurring in a continuum as it is well known, and an analysis model obtained by dividing a continuum into a plurality of finite elements. That is, the analysis model is used in an analyzing process in the stress distortion analysis unit 12. The element damage evaluation unit 13 and the element rigidity change unit 14 also refer to the analysis model.

Figure 7:
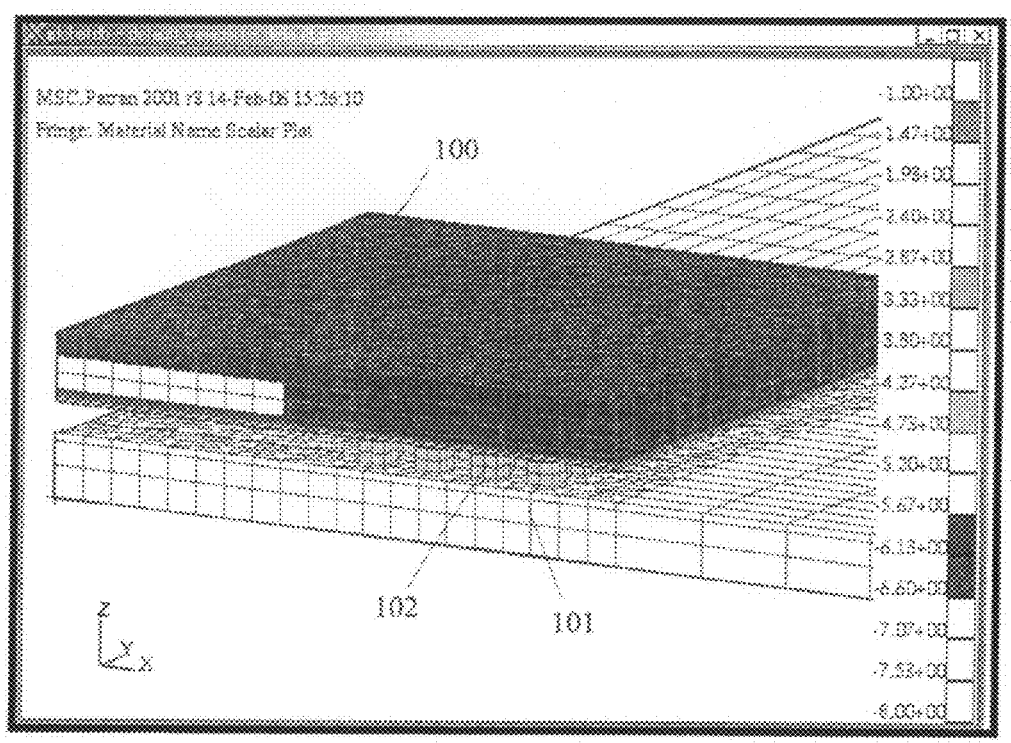
FIG. 7 shows an analysis model of a BGA package.
Figure 8:
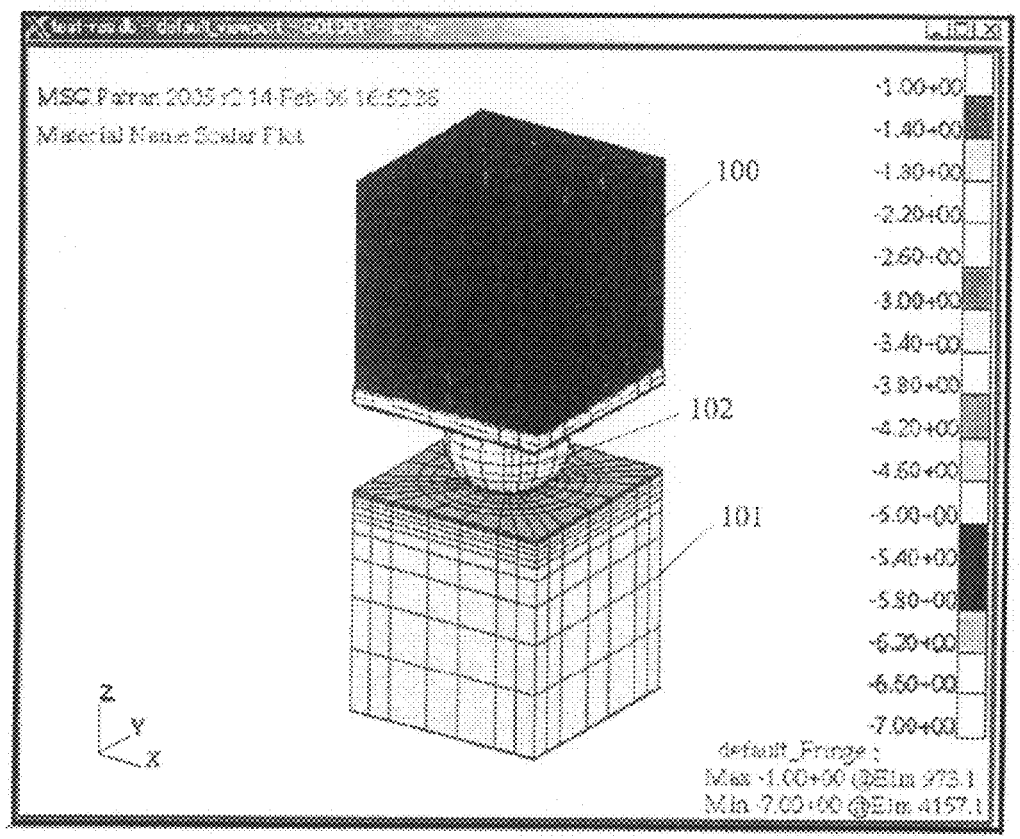
FIG. 8 is a partially enlarged view of an analysis model of the BGA package.
Figure 15:
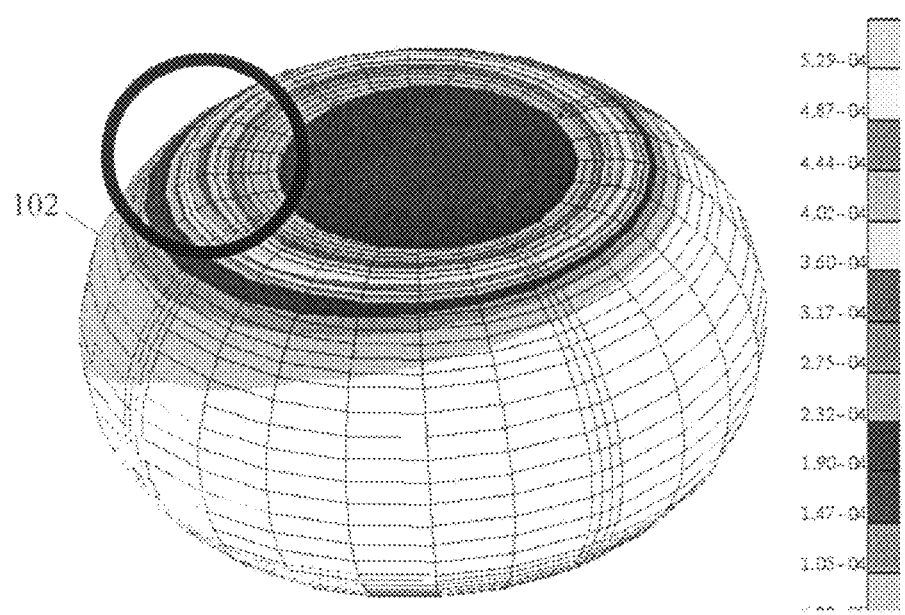
FIG. 15 shows an analysis model of a soldered portion.

For example, the analysis model is generated for the soldered portion between an electronic component and a substrate. In this case, the soldered portion of the electronic component comprises a continuum. The generation unit 11 generates an analysis model of the soldered portion based on the information about an electronic component, the information about a substrate, the position information about a soldered portion, the information about a load cyclically applied to the soldered portion, and the information about the material of the soldered portion. FIGS. 7, 8, and 15, described later, show such an analysis model of the soldered portion.

According to the present invention, as described later, the analysis model is generated, and is not regenerated later (updated). That is, in the present invention, an analysis model is generated only once for one analysis object. Thus, the analyzing process does not require several hours to several days.

The stress distortion analysis unit (hereinafter referred to as an analysis unit) 12 analyzes a stress and a distortion occurring in each of a plurality of finite elements of a continuum by a load for each cycle of the load cyclically applied to the continuum using the analysis model (a stress and distortion analysis is performed). A result of the analysis by the analysis unit 12 is transmitted to the element damage evaluation unit 13. A predetermined number of cycles of a load for a simulation are applied to the continuum. A stress distortion analysis is performed for each of the predetermined number of cycles. The load is, for example, a temperature, a mechanical pressure, and so on.

Specifically, the analysis unit 12 obtains a cumulative equivalence creep distortion value and/or a cumulative equivalence plasticity distortion value as the stress distortion for each of a plurality of finite elements of a continuum. In this description, "cumulative equivalence" or "cumulative" creep distortion value refers to a value obtained by accumulating a creep distortion value calculated in each cycle before the relevant cycle. The same holds true with a plasticity distortion value.

In the present invention, an analysis model is not generated again. Therefore, practically an analyzing process can be performed by the analysis unit 12 concurrently with the generation of an analysis model. Thus, the processing time can be further shortened.

Figure 2:
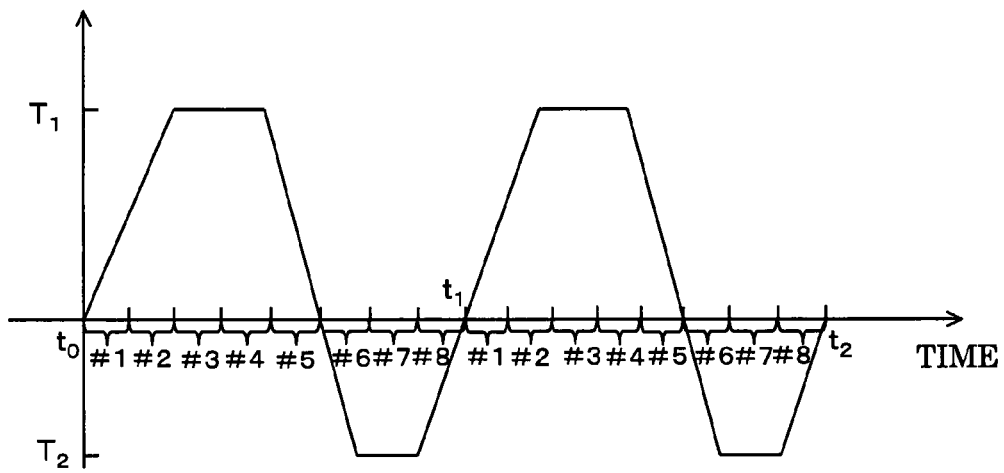
FIG. 2 shows an example of a temperature cycle applied to a continuum.
Figure 9:
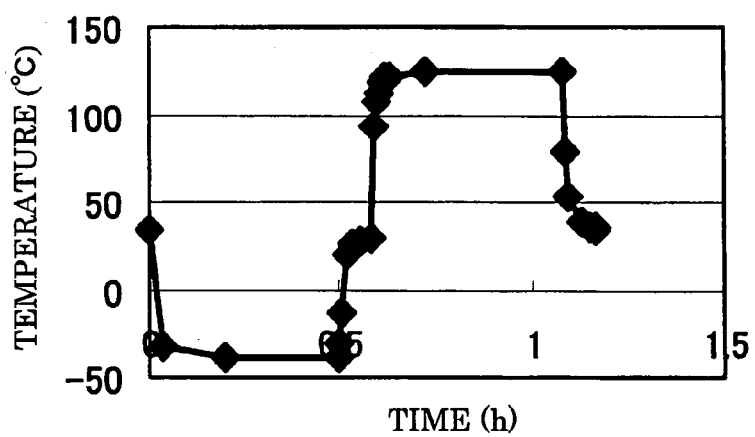
FIG. 9 shows a temperature cycle applied to a soldered portion.
Figure 10:
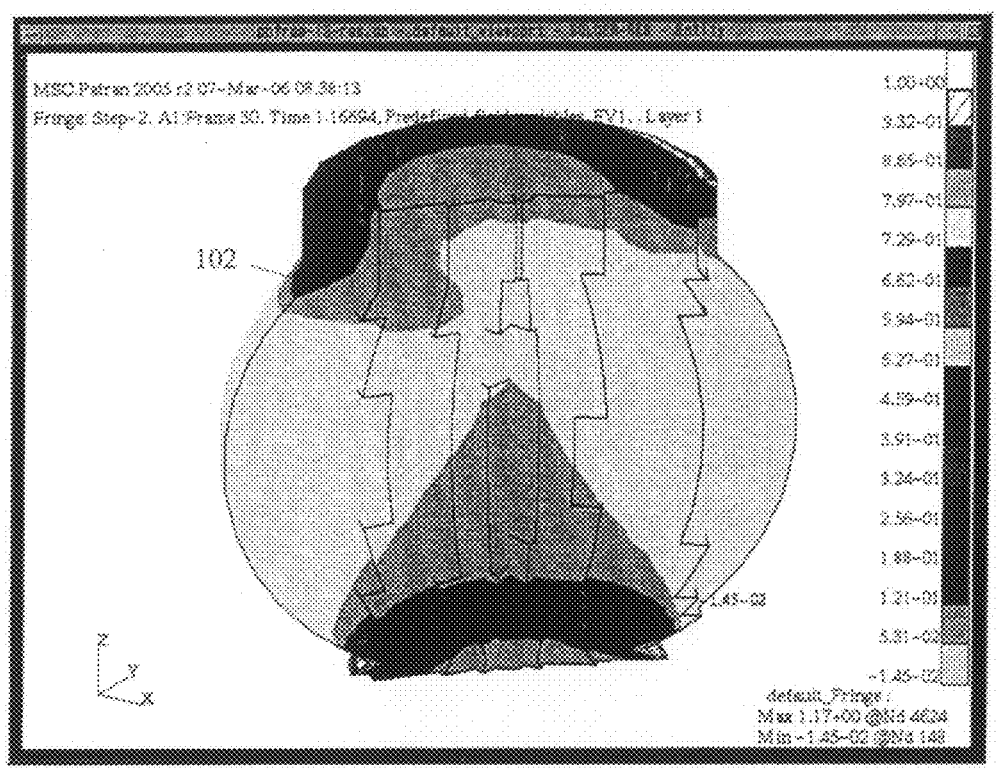
FIGS. 10, 11, 12, and 13 show a result of a crack growth evaluation simulation.
Figure 11:
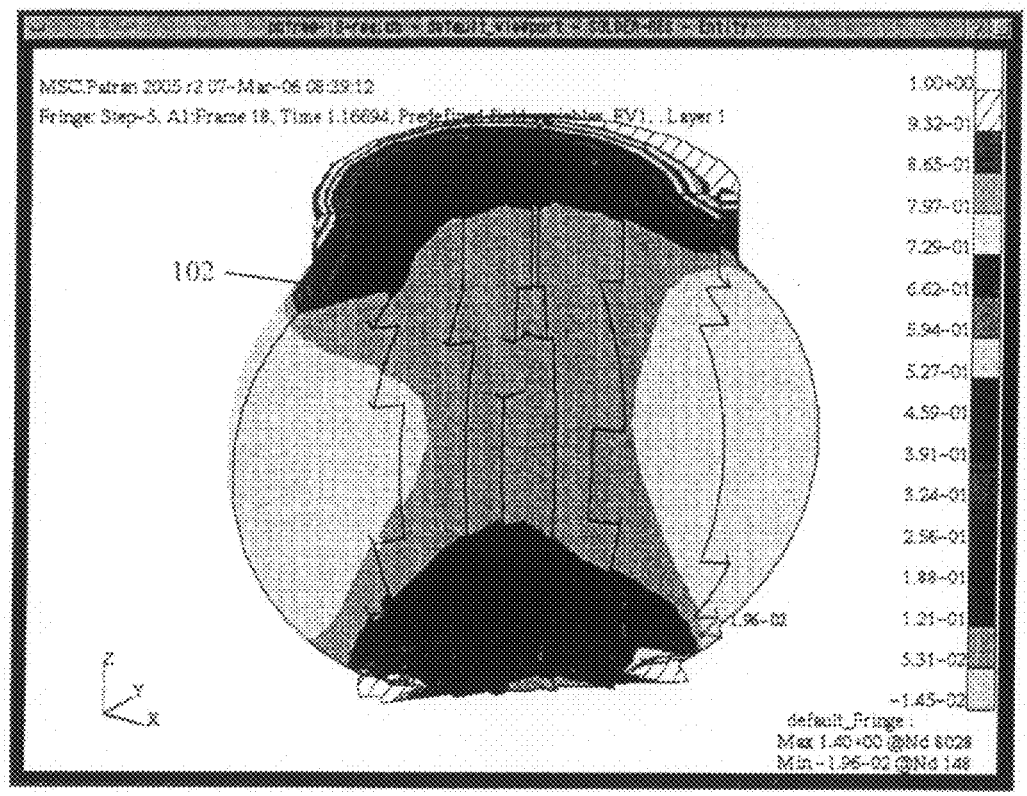
Figure 12:
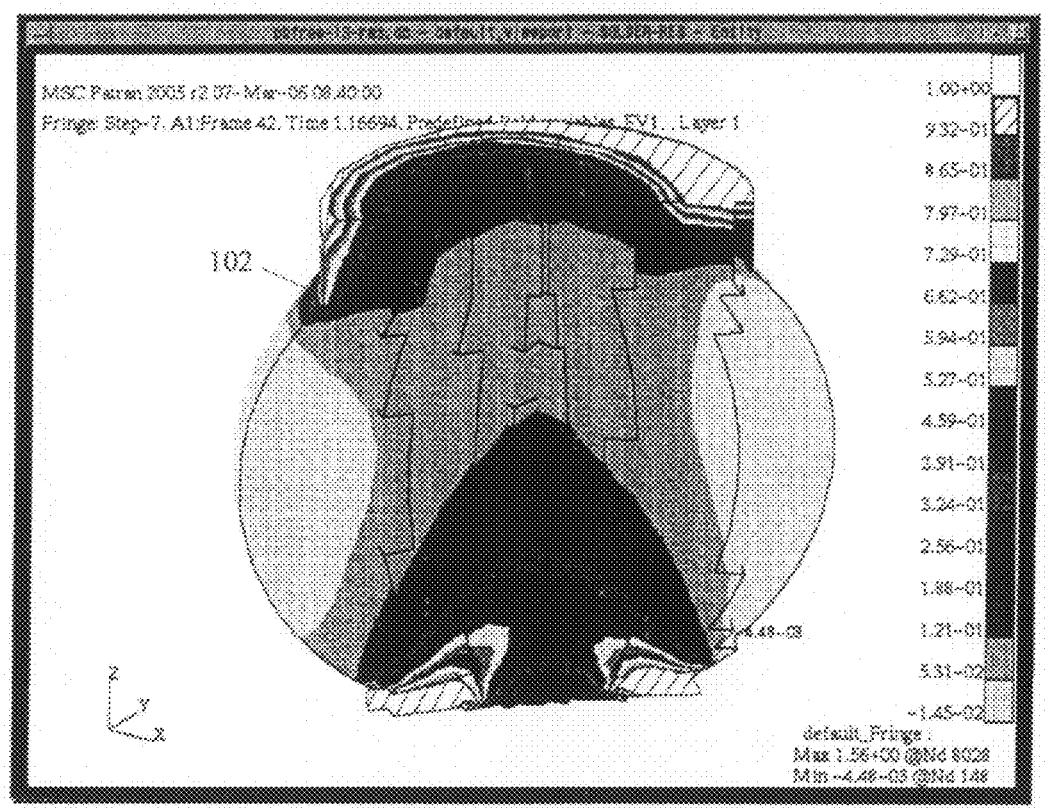
Figure 13:
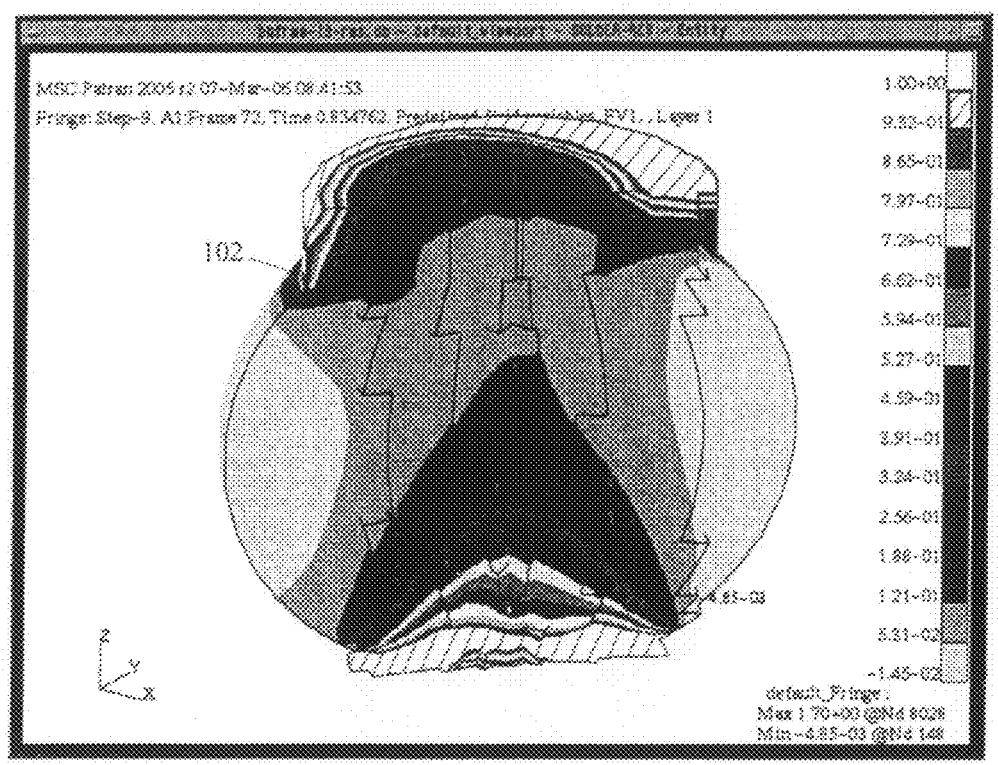

FIG. 2 shows an example of a temperature cycle as an example of a cycle of a load applied to a continuum. FIG. 2 only shows the first temperature cycle (first cycle) and the second temperature cycle (second cycle) in a predetermined number of times of temperature cycles cyclically applied to the continuum. In this example, the first and second cycles are the cycles having the same load gradient, but they can be different cycles. Since the third temperature cycle (third cycle) and the subsequent cycles are similar to the first and/or second cycle, they are not shown in the attached drawings. FIG. 9 shows an example of a practical load cycle (temperature cycle).

In FIG. 2, the first temperature cycle (first cycle) spans time $t_0$ to time $t_1$, and the second temperature cycle (second cycle) spans time $t_1$ to time $t_2$. In the example shown in FIG. 2, the continuum is heated up to the temperature $T_1$ in each temperature cycle, and maintained at the temperature $T_1$ for a predetermined time. The continuum is cooled down to the temperature $T_2$, and maintained at the temperature $T_2$ for a predetermined time. In FIG. 2, #1 to #8 designate time increments. The time increment refers to a time as a process unit of a stress distortion analyzing process by the generation unit 11 and a calculating process of a cumulative damage value D by the element damage evaluation unit 13.

In the load cycle cyclically applied to the continuum, the cycle currently to be processed in the stress distortion analyzing process, a damage evaluating process and/or a rigidity changing process is referred to as a "current cycle". A cycle immediately before the current cycle is referred to as a "preceding cycle", and a cycle immediately after the current cycle is referred to as a "next cycle".

The element damage evaluation unit (hereinafter referred to as an evaluation unit) 13 evaluates damage by a distortion occurring in the continuum for each of the plurality of finite elements of the continuum in each load cycle cyclically applied to the continuum using the analysis model based on a result of a analysis (referred to as an analysis result) by the analysis unit 12. That is, the evaluation unit 13 calculates a cumulative nonlinear distortion value for each of the finite elements of the continuum, calculates a nonlinear distortion amplitude value based on the cumulative nonlinear distortion value, calculates a damage value using the Manson-Coffin law based on the nonlinear distortion amplitude value, calculates a cumulative value of the damage value (cumulative damage value D) based on the damage value, and compares the cumulative damage value D with a predetermined threshold. An result of an evaluation (referred to as an evaluation result) by the evaluation unit 13 is transmitted to the element rigidity change unit 14.

Specifically, as it is well known, the evaluation unit 13 first calculates and stores a cumulative nonlinear distortion value of a finite element based on a cumulative equivalence creep distortion value and/or cumulative equivalence plasticity distortion value of each of the finite elements of the continuum. To store the calculated cumulative nonlinear distortion value, the evaluation unit 13 includes a storage unit (not shown in the attached drawings).

Figure 3:
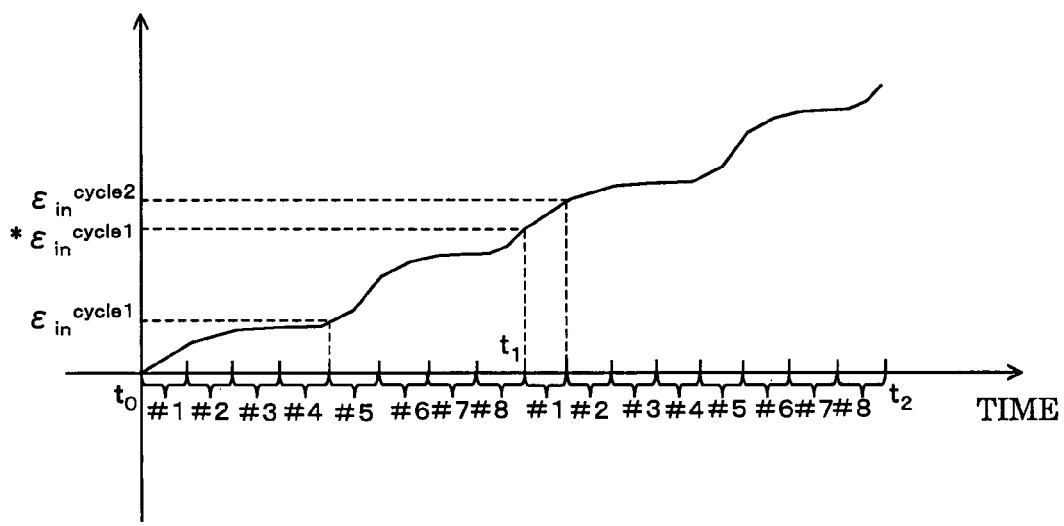
FIG. 3 shows an example of a cumulative nonlinear distortion value.

FIG. 3 shows an example of a cumulative nonlinear distortion value sequentially calculated by the evaluation unit 13 with the lapse of time. The example shows a cumulative nonlinear distortion value when the temperature cycle shown in FIG. 2 is applied to the continuum. As shown in FIG. 3, the cumulative nonlinear distortion value increases with time. In FIG. 3, $\epsilon_{in}^{cycle1}$ indicates a cumulative nonlinear distortion value being calculated (at the time point that the calculating process on the damage value for the time increment #4 in the first cycle is terminated) for the first cycle. $\epsilon_{in}^{cycle2}$ indicates a cumulative nonlinear distortion value being calculated (at the time point that the calculating process on the damage value for the time increment #1 in the second cycle is terminated) for the second cycle. $*\epsilon_{in}^{cycle1}$ indicates a final cumulative nonlinear distortion value (final cumulative nonlinear distortion value) for the first cycle.

Next, the evaluation unit 13 calculates the nonlinear distortion amplitude value for each of the plurality of finite elements of the continuum based on the stored cumulative nonlinear distortion value, and calculates a damage value of the relevant finite element based on the calculated nonlinear distortion amplitude value using the Manson-Coffin law. The damage value is calculated for each of the load cycles. The damage value is calculated for each load cycle. The value obtained by accumulating the damage values up to the corresponding cycle (current cycle) is a cumulative damage value D.

As a nonlinear distortion amplitude value, for example, half the cumulative nonlinear distortion value is used. The value is different in a precise sense from a cumulative nonlinear distortion value, but does not largely affect a calculation result of the cumulative damage value D. By using half the cumulative nonlinear distortion value as the nonlinear distortion amplitude value, the processing time required to calculate the nonlinear distortion amplitude value can be shortened.

Next, the evaluation unit 13 calculates a cyclic fatigue life count of a relevant finite element by applying the Manson-Coffin law expressed by the following equation to the nonlinear distortion amplitude value of the relevant finite element. The value is calculated for each load cycle.

$$Nf_i = C \cdot (\Delta\epsilon_i)^{-n} \quad (1 \leq i \leq k) \qquad \text{(equation 2)}$$

In the equation 2 above, $Nf_i$ indicates the cyclic fatigue life count on the i-th load cycle (i-th cycle). $\Delta\epsilon_i$ indicates a nonlinear distortion amplitude value in the i-th cycle. C and n are constants. When the term of the multiplier in the equation 1 above is developed, the equation of multiplying the −n-th power of the nonlinear distortion amplitude value by a constant as expressed by the equation 2 is obtained.

The evaluation unit 13 calculates $i/Nf_i = 1/C \cdot (\Delta\epsilon_i)^{-n}$ as a damage value in the i-th cycle. That is, it is an inverse of the cyclic fatigue life count. Furthermore, the evaluation unit 13 calculates the cumulative damage value D by adding up the damage values up to the relevant cycle (current cycle) using the equation 3 below, and stores the cumulative damage value D.

$$D = 1/C \cdot (\Delta\epsilon_1)^{-n} + 1/C \cdot (\Delta\epsilon_2)^{-n} + \ldots + 1/C \cdot (\Delta\epsilon_k)^{-n} \qquad \text{(equation 3)}$$

Furthermore, the evaluation unit 13 compares the cumulative damage value D stored in the storage unit with a predetermined threshold (for example, 1). The threshold can be empirically determined. The result of the comparison is transmitted to an element rigidity change unit 14.

The element rigidity change unit (hereinafter referred to as a change unit) 14 changes (reduces) the rigidity of each of the plurality of finite elements of the continuum based on the evaluation result of the damage by the evaluation unit 13. In the present invention, for example, a Young's modulus or a yield stress is used as the rigidity of a finite element.

Specifically, when the evaluation unit 13 determines that the cumulative damage value D is equal to or more than the threshold, the change unit 14 reduces the rigidity of the finite element down to a predetermined value. When the evaluation unit 13 determines that the cumulative damage value D is not more than the threshold, then the change unit 14 does not change the rigidity of the finite element, but holds the value.

The change unit 14 reduces the rigidity of the finite element down to a value close to 0 (for example, 1/100 of the initial value of the rigidity of the finite element). That is, the rigidity of the finite element is not set to 0. Thus, in the stress distortion analyzing process in the next cycle to the current cycle of the load cycles, for example, the cumulative equivalence creep difference value and the cumulative equivalence plasticity distortion value can be prevented from being extremely large numbers (unreasonable value).

The change unit 14 does not reduce again in the next and subsequent cycles to the current cycle the value of the rigidity in the crack growth evaluating process on the finite element whose rigidity is once reduced to the predetermined value in a crack growth evaluating process in the current cycle of the load cycles.

Thus, after the change unit 14 has changed the rigidity of the finite element, the stress distortion analysis unit 12 analyzes the stress and the distortion occurring in the next cycle of the current cycle of the load cycles for each of the plurality of finite elements for the continuum for which the rigidity of the finite element has been changed. Thus, the change of the rigidity based on the cumulative damage value D is reflected in the stress distortion analyzing process by the stress distortion analysis unit 12.

The crack growth display unit 15 displays the growth of a crack occurring in the continuum using an analysis model based on a result of an evaluation of the damage by the evaluation unit 13. The growth of the crack is displayed, for example, by displaying the cumulative damage value D for each of the plurality of finite elements of the continuum. Thus, the growth of the crack is displayed in, for example, FIGS. 10 to 13 described later.

Furthermore, the crack growth display unit 15 displays the growth of a crack occurring in the continuum in each of predetermined one or more load cycles. That is, the display of the growth of the crack by the crack growth display unit 15 is updated in each of one or more cycles (for example, 10 cycles). The cycle count in updating the display is predetermined (the same holds true in the following descriptions).

Furthermore, the crack growth display unit 15 calculates and displays the length of the crack occurring in the continuum for each of predetermined one or more load cycles. The length of the crack is calculated based on the information about the area including the finite element having the cumulative damage value in the analysis model of the continuum equal to or exceeding a predetermined threshold. The length of the crack occurring in the continuum is shown in, for example, FIG. 14.

Furthermore, the crack growth display unit 15 calculates the complete fracture life from the occurrence of a crack in the continuum to the final fracture based on information on the length of the crack and dimension of the continuum. The complete fracture life is calculated in each of the predetermined one or more load cycles as described above.

In the example shown in FIG. 1 described above, a half value of the cumulative nonlinear distortion value is used as a value of nonlinear distortion amplitude. Alternatively, the nonlinear distortion amplitude value can also be calculated as follows.

That is, the evaluation unit 13 subtracts the cumulative nonlinear distortion value in the cycle immediately before the current cycle from the cumulative nonlinear distortion value in the current cycle of the load cycles for each of the plurality of finite elements of the continuum. Thus, the nonlinear distortion amplitude value in the current cycle is calculated in each of the plurality of finite elements of the continuum. That is, the difference between the cumulative nonlinear distortion value in the current cycle of the load cycles and the cumulative nonlinear distortion value in the cycle immediately before the current cycle is the nonlinear distortion amplitude value in the current cycle.

Furthermore, the nonlinear distortion amplitude value can also be calculated as follows.

That is, the evaluation unit 13 obtains an average value of the cumulative nonlinear distortion value based on the cumulative nonlinear distortion value in the load cycle in a predetermined order and the cycle count up to the load cycle in the predetermined order for each of the plurality of finite elements of the continuum. Furthermore, the evaluation unit 13 calculates the nonlinear distortion amplitude value in the load cycle in the predetermined order based on the average value.

In this case, there is no necessity for the process of storing the cumulative nonlinear distortion value in each load cycle in the storage unit. Furthermore, there is no necessity for the process of the evaluation unit 13 subtracting the cumulative nonlinear distortion value in the cycle immediately before the current cycle of the load cycles from the cumulative nonlinear distortion value in the current cycle of the load cycles.

In the example shown in FIG. 1, the cumulative damage value D is calculated by the equation 3. Alternatively, the cumulative damage value D can also be calculated as follows.

That is, the evaluation unit 13 calculates the damage value obtained when adding the load equal to the load in the current cycle of the load cycles to the continuum a predetermined number of times by multiplying the damage value in the current cycle by a predetermined value for each of the plurality of finite elements of the continuum. The predetermined value corresponds to the predetermined number of times. That is, a predetermined value in this case is a cycle count added to the continuum. The evaluation unit 13 defines the calculated damage value as a cumulative damage value obtained when the load cycles are repeated the predetermined number of times for each of the plurality of finite elements of the continuum.

For example, assume that the current cycle is the fifteenth cycle, and the predetermined value is 100. In this case, the evaluation unit 13 calculates the damage value in the fifteenth cycle, and multiplies the value by the predetermined value of 100 (that is, the damage value is multiplied by 100). Thus, the cumulative damage value D in the 1500th cycle is calculated. Thus, the calculating time of the cumulative damage value D can be shortened.

Furthermore, the cumulative damage value D can be calculated as follows.

That is, the evaluation unit 13 calculates the change rate of the damage value for each of the plurality of finite elements of the continuum. The evaluation unit 13 calculates the damage value obtained when adding the load equal to the load in the current cycle of the load cycles to the continuum a predetermined number of times corresponding to the change rate by multiplying the damage value in the current cycle by a predetermined value. The predetermined value corresponds to the predetermined number of times. The predetermined number in this case is also a cycle count. A predetermined value corresponding to the change rate is stored in a storage unit in advance, and is determined based on the correspondence information about the change rate of the damage value for each of the plurality of finite elements of the continuum and the predetermined value. The evaluation unit 13 defines the calculated damage value as a cumulative damage value in the case where the load cycle is repeated the number of times of the predetermined value for each of the plurality of finite elements of the continuum.

In this case, the predetermined value corresponding to the change rate is prepared as, for example, the first value N1 and the second value N2. The first value N1 corresponds a load cycle having a low change rate of a damage rate, and assumed as a large value. The second value N2 corresponds a load cycle having a high change rate of a damage rate, and assumed as a small value. As predetermined values, a plurality of values can be prepared.

When the change rate of a damage rate is small, the evaluation unit 13 calculates a damage value obtained when the same load as the load in the corresponding cycle is added to the continuum N1 times by multiplying the first value N1 by the damage value in the corresponding cycle. The evaluation unit 13 calculates the damage value obtained when the same load as the load in the corresponding cycle is added to the continuum N2 times by multiplying the damage value in the corresponding cycle by the second value N2 when the change rate of the damage rate is large.

As described above, the cumulative damage value in the case where the load cycle is repeated a predetermined number of times can be obtained without calculating the damage value in each load cycle. Therefore, the calculating time of the cumulative damage value can be shortened. Additionally, a cumulative damage value is more correctly calculated by using a plurality of predetermined values depending on the change rate.

Furthermore, the cumulative damage value D can be calculated as follows. That is, in place of the change rate of the damage rate, the cumulative damage value D can be obtained based on the nonlinear distortion amplitude value as described above.

In short the evaluation unit 13 calculates a damage value obtained when the same load as the load in the current cycle of the load cycles is added to the continuum the number of times of a predetermined value corresponding to the nonlinear distortion amplitude value for each of the plurality of finite elements of the continuum by multiplying the damage value in the current cycle by the predetermined value. The predetermined value corresponding to the nonlinear distortion amplitude value is determined based on the correspondence information between the nonlinear distortion amplitude of each damage value of the plurality of finite elements of the continuum and the predetermined value stored in a storage unit in advance.

In this case, for example, the first value N1 corresponds to a cycle of a load having a low nonlinear distortion amplitude value, and is assumed as a large value. The second value N2 corresponds to a cycle of a load having a high nonlinear distortion amplitude value, and is assumed as a small value. As the predetermined value, a plurality of values can be prepared.

The evaluation unit 13 calculates a damage value using the first value N1 or the second value N2, and defines them as cumulative damage values depending on the level of the nonlinear distortion amplitude value as in the case described above. Thus, an effect similar to that in the above-mentioned case can be obtained.

Figure 4:
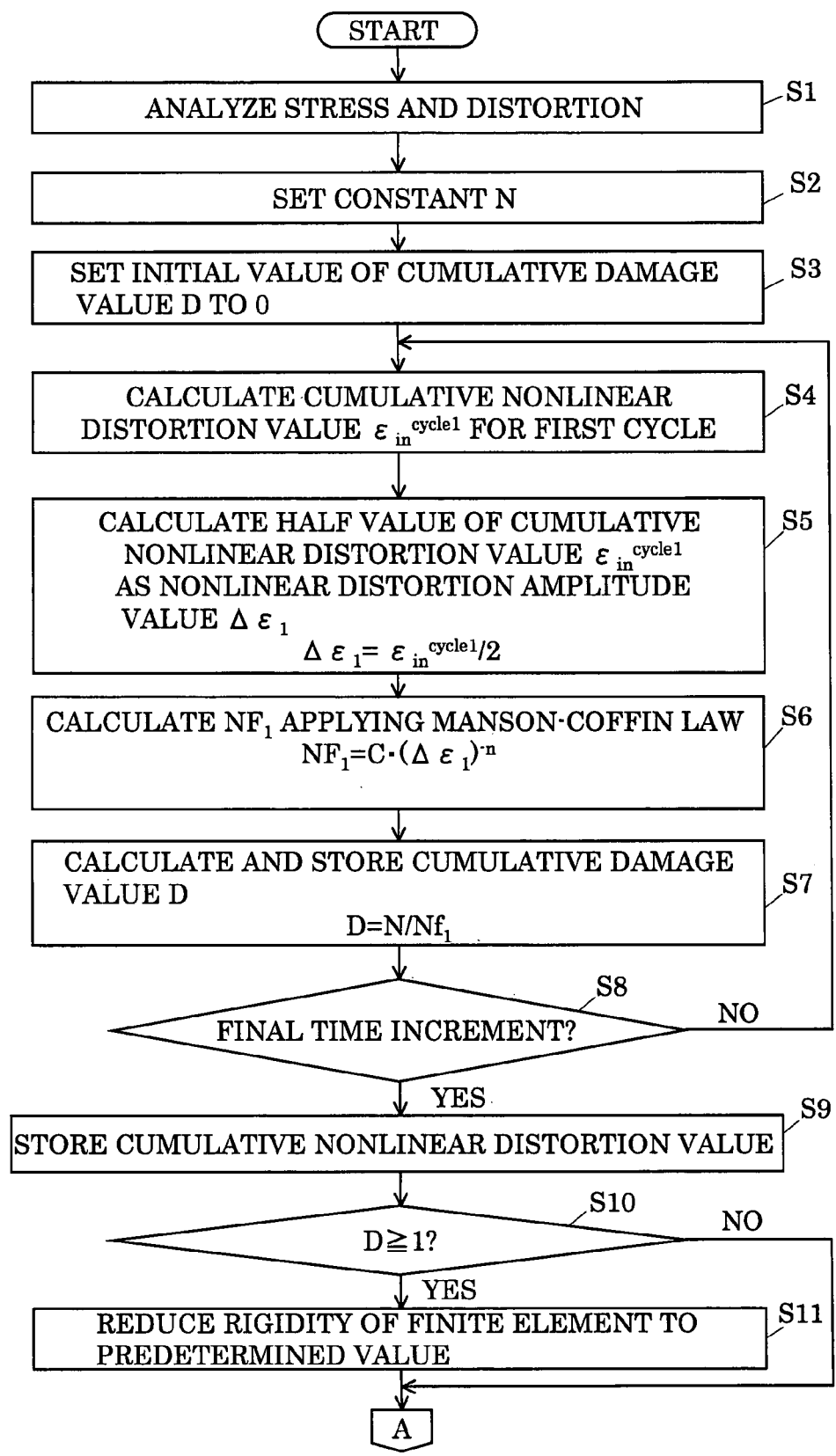
FIGS. 4 and 5 show an example of a flowchart of a crack growth evaluation process according to the present invention.
Figure 5:
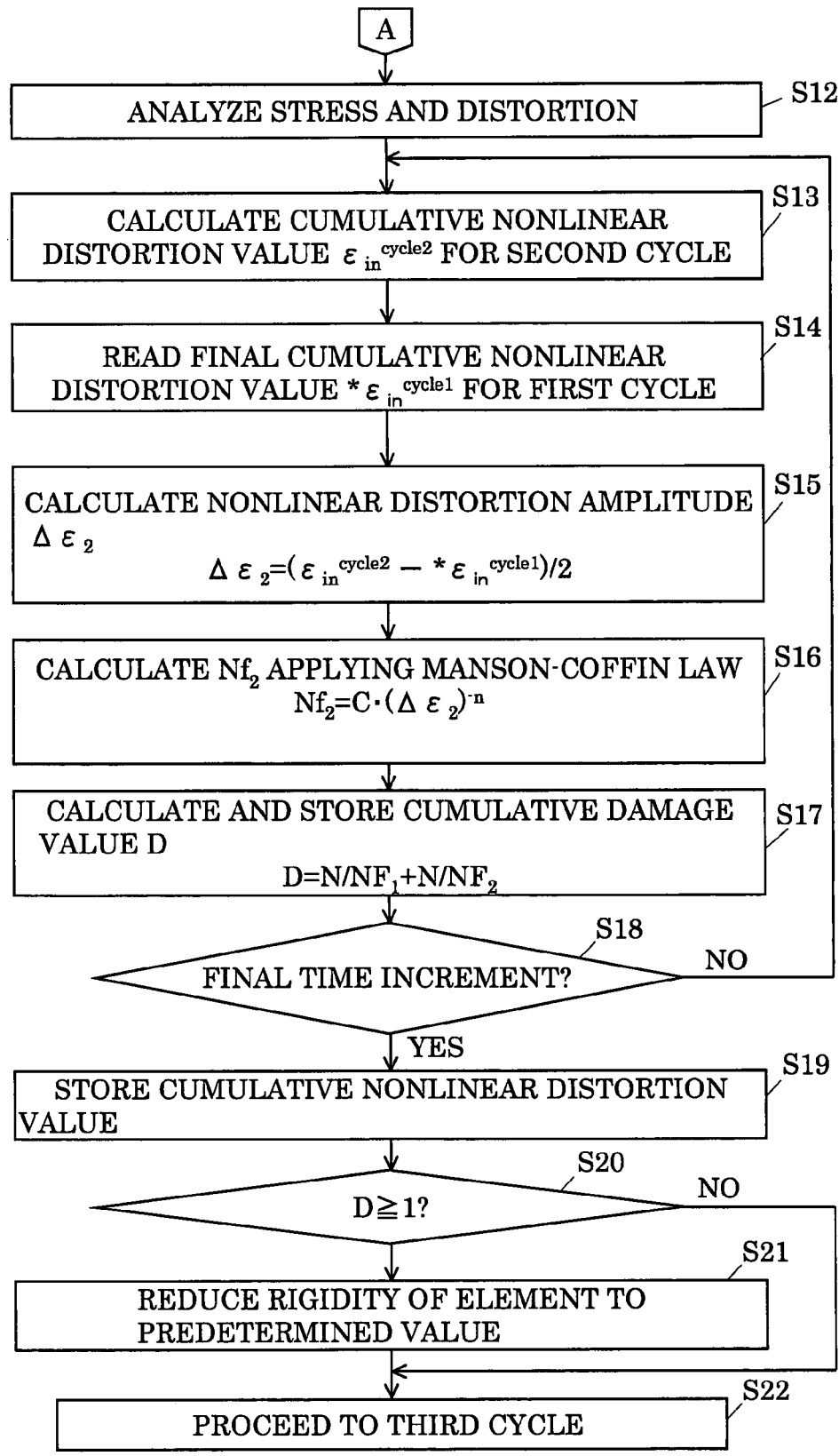

FIGS. 4 and 5 show examples of the crack growth evaluating process flow according to the present invention, and show a flowchart of the crack growth evaluating process when a temperature cycle is applied to the continuum. Steps S1 to S11 shown in FIG. 4 are the crack growth evaluating process in the first cycle in FIG. 2. Steps S12 to S21 shown in FIG. 5 are the crack growth evaluating process in the second cycle shown in FIG. 2. The crack growth evaluating process in and after the third cycle is similar to that of the crack growth evaluating process in the second cycle.

In step S1, the stress distortion analysis unit 12 performs stress distortion analysis in the first cycle on each of the plurality of finite elements (all finite elements) of the continuum. Next, in step S2, the evaluation unit 13 sets a constant N. In step S3, the evaluation unit 13 sets the initial value of the cumulative damage value D to 0. Then, the evaluation unit 13 executes processes in the following steps S4 to S11 for each of the plurality of finite elements of the continuum.

That is, in step S4, the evaluation unit 13 calculates the cumulative nonlinear distortion value $\epsilon_{in}^{cycle1}$ for the first cycle based on the stress distortion analysis result in the step S1. That is, the cumulative nonlinear distortion value $\epsilon in^{cycle1}$ obtained when the calculating process on the damage value is completed on the time increment #4 in the first cycle shown in FIG. 3 is calculated.

In step S5, the evaluation unit 13 calculates a half value of the cumulative nonlinear distortion value $\epsilon_{in}^{cycle1}$ as a nonlinear distortion amplitude value $\Delta\epsilon_1$. In step S6, the evaluation unit 13 applies the Manson-Coffin law $(Nf_1=C\cdot(\Delta\epsilon_1)^{-n})$ according to the equation 2, and calculates the cyclic fatigue life count $Nf_1$. Furthermore, in step S7, the evaluation unit 13 calculates the cumulative damage value D by multiplying the value $1/Nf_1$ by the constant N, and stores the cumulative damage value D in the storage unit.

Next, in step S8, the evaluation unit 13 determines whether or not the process on the final time increment has been completed. When the evaluation unit 13 determines that the process has not been completed, control is returned to the step S4. When the process is terminated, the evaluation unit 13 stores the cumulative nonlinear distortion value as the final cumulative nonlinear distortion value $\epsilon_{in}^{cycle1}$ for the first cycle in step S9.

Next, in step S10, the evaluation unit 13 determines whether or not the cumulative damage value D is 1 or more. When the cumulative damage value D is not 1 or more, the process proceeds to step S12 shown in FIG. 5. When the cumulative damage value D is 1 or more, the change unit 14 reduces the rigidity of each of the finite elements of the continuum to a predetermined value in step S11, and the process proceeds to step S12 shown in FIG. 5.

In the step S12 shown in FIG. 5, the analysis unit 12 performs a stress distortion analysis in the second cycle on each of the plurality of finite elements of the continuum, and the process in steps S13 to S21 is performed on each of the plurality of finite elements of the continuum.

That is, in the step S13, the evaluation unit 13 calculates the cumulative nonlinear distortion value $\epsilon_{in}^{cycle2}$ for the second cycle based on the result of the stress distortion analysis. That is, the cumulative nonlinear distortion value $\epsilon_{in}^{cycle2}$ obtained when the process of calculating the damage value on the time increment #1 in the second cycle shown in FIG. 3 is calculated.

Next, in the step S14, the evaluation unit 13 reads the final cumulative nonlinear distortion value $\epsilon_{in}^{cycle1}$ for the first cycle from the storage unit. In step S15, the evaluation unit 13 calculates the half value of the difference between $\epsilon_{in}^{cycle2}$ and $\epsilon_{in}^{cycle1}$ as the nonlinear distortion amplitude value $\Delta\epsilon_2$. Furthermore, in step S16, the evaluation unit 13 applies the Manson-Coffin law $(Nf_2=C\cdot(\Delta\epsilon_2)^{-n})$ according to the equation 2 to the nonlinear distortion amplitude value $\Delta\epsilon_2$, and calculates the cyclic fatigue life count $Nf_2$. Furthermore, in step S17, the evaluation unit 13 calculates the cumulative damage value D $(D=N/Nf_1+N/Nf_2)$ and stores the cumulative damage value.

Next, in step S18, the evaluation unit 13 determines whether or not the process on the final time increment has been completed. When the process has not been completed, control is returned to the step S13. When the evaluation unit 13 determines that the process has been completed, the evaluation unit 13 stores a cumulative nonlinear distortion value in step S19.

Next, in step 20, the evaluation unit 13 determines whether or not the cumulative damage value D is 1 or more. When the cumulative damage value D is not 1 or more, the process proceeds to step S22. When the cumulative damage value D is 1 or more, then the change unit 14 reduces the rigidity of each of the finite elements of the continuum to a predetermined value in step S21, and the process proceeds to the crack growth evaluating process for the third cycle in step S22. For example, after the step S21, the crack growth display unit 15 displays the cumulative damage value of each of the finite elements of the continuum as the information about the growth of a crack occurring in the continuum.

In the examples shown in FIGS. 4 and 5, the finite elements whose rigidity is reduced to a predetermined value in the first cycle (refer to the step S11 shown in FIG. 4) is not deleted from an analysis model, and the elements are to be treated in the process of calculating the cumulative damage value D in the second and subsequent cycles (refer to step S17 shown in FIG. 5). Since the finite elements whose rigidity is reduced to a predetermined value are not deleted from an analysis model, it can be not necessary to perform the process of re-generating an analysis model of the continuum.

In the examples shown in FIGS. 4 and 5, the finite elements whose rigidity has been reduced to a predetermined value in the first cycle is to be processed in the stress distortion analysis in the second cycle (refer to the step S11 shown in FIG. 4, and the step S12 shown in FIG. 5). The analysis result in the second cycle is naturally different from the analysis result of the finite elements whose rigidity has not been reduced in the first cycle. Since the cumulative damage value D is calculated based on the analysis result (refer to the step S17 shown in FIG. 5), the reduction in rigidity of a finite element affects the cumulative damage value D of another finite element. Thus, it can be not necessary to perform the process of regenerating an analysis model of a continuum only by reducing the rigidity to a predetermined value without deleting the finite element from the analysis model.

Figure 6:
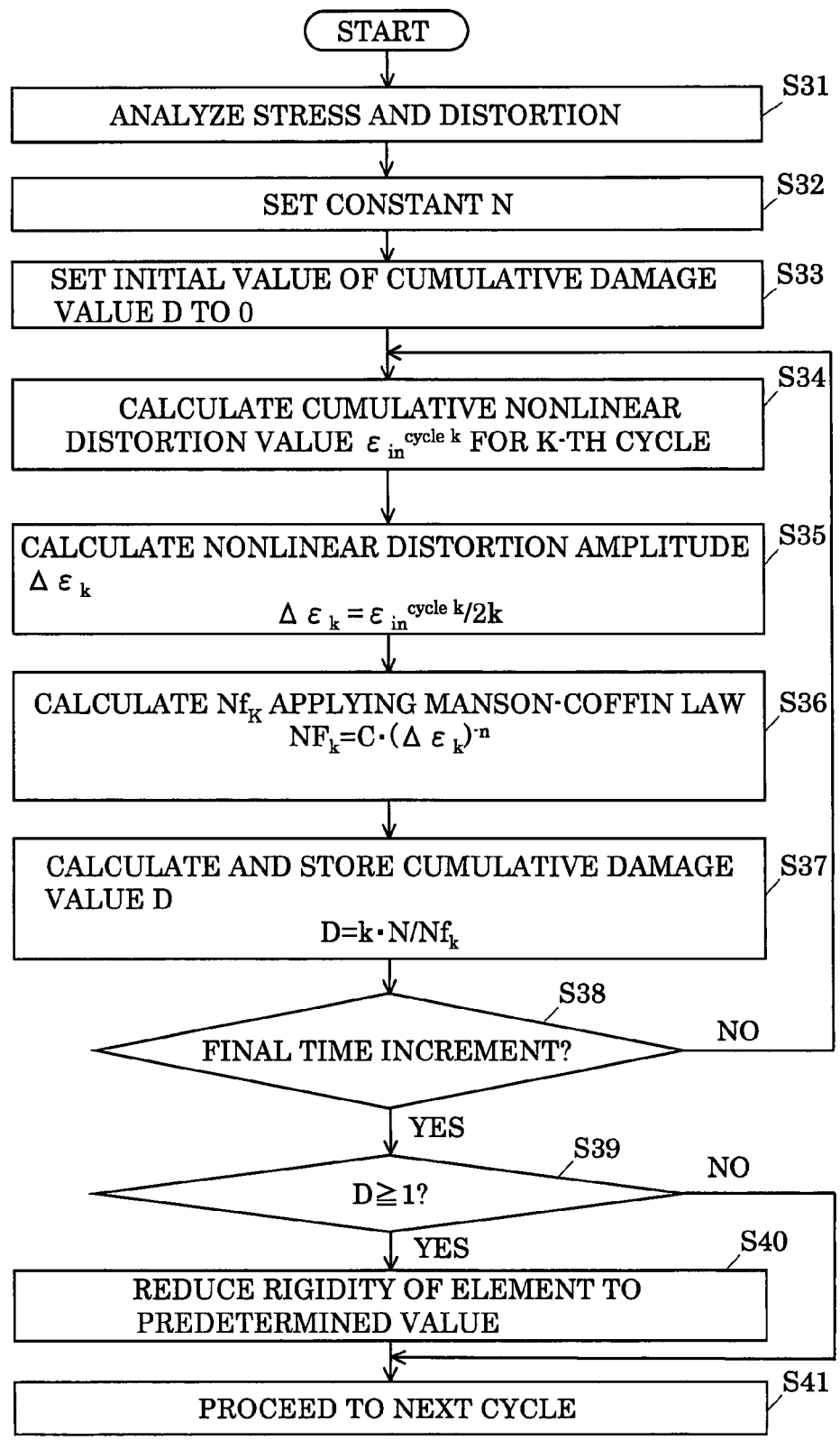
FIG. 6 shows another example of a flowchart of the crack growth evaluation process according to the present invention.

FIG. 6 shows another example of a flowchart of the crack growth evaluating process according to the present invention. In this example, when a temperature cycle is added to a continuum, the crack growth evaluating process is performed without distinguishing between the first and second cycles as in the process shown in FIGS. 4 and 5.

In step S31, the stress distortion analysis unit 12 performs a stress distortion analysis on a predetermined k-th cycle on each of the plurality of finite elements of the continuum. Furthermore, in step S32, the evaluation unit 13 sets a constant N. In step S33, the evaluation unit 13 sets the initial value of the cumulative damage value D to 0. Then, the subsequent processes S34 to S40 are performed on each of the plurality of finite elements of the continuum.

That is, in the step S34, the evaluation unit 13 calculates the cumulative nonlinear distortion value $\epsilon_{in}^{cyclek}$ for the k-th cycle based on the stress distortion analysis result in step S31. Using the calculated value, the evaluation unit 13 calculates $\epsilon_{in}^{cyclek}/2k$ as the nonlinear distortion amplitude value $\Delta\epsilon_k$ for the k-th cycle in step S35. Furthermore, in step S36, the evaluation unit 13 applies the Manson-Coffin law ($Nf_k=C\cdot(\Delta\epsilon_k)^{-n}$) according to the equation 2 to the nonlinear distortion amplitude value $\Delta\epsilon_k$, and calculates the cyclic fatigue life count $Nf_k$. Using the result, the evaluation unit 13 calculates the cumulative damage value D ($D=k\cdot N/Nf_k$), and stores the cumulative damage value D in step S37.

Next, in step S38, the evaluation unit 13 determines whether or not the process of calculating the cumulative damage value D on the final time increment has been completed. When the evaluation unit 13 determines that the process has not been completed, control is returned to the step S34. When the evaluation unit 13 determines that the process is terminated, the evaluation unit 13 determines whether or not the cumulative damage value is 1 or more in step S39. When the evaluation unit 13 determines that the cumulative damage value is not 1 or more, the process proceeds to step S41. When the evaluation unit 13 determines that the cumulative damage value D is 1 or more, the change unit 14 reduces the rigidity of each of the plurality of finite elements of the continuum to a predetermined value in step S40, and the process proceeds to the crack growth evaluating process on the next cycle in step S41.

Next, a result of a specific simulation performed on the soldered portion of an electronic component by the crack growth evaluation apparatus 1 according to the present invention is described below with reference to FIGS. 7 to 14.

In this example, the crack growth evaluation apparatus 1 performs a crack growth simulation on the soldered portion of a BGA (ball grid array) package. In the crack growth simulation, the crack growth evaluation apparatus 1 sets, for example, a predetermined value (cycle count) to 100, performs a crack growth evaluating process on the temperature cycle for 15 cycles, and evaluates the growth of a crack obtained when the temperature cycle for 1500 cycles is added to the soldered portion.

FIG. 7 shows an analysis model of a BGA package generated by the crack growth evaluation apparatus 1 in the crack growth evaluating simulation. The generation unit 11 of the crack growth evaluation apparatus 1 generates an analysis model including an electronic component 100 (semiconductor chip), an implementation substrate 101, and a soldered portion 102. Actually, FIG. 7 shows a screen displayed on a display by the display unit 15. In FIG. 7, the rightmost portion on the screen is a bar colored depending on the number of a finite element of the analysis model to display the finite element of the analysis model (the same holds true in FIG. 8).

FIG. 8 is an enlarged view of a part of the analysis model of the BGA package shown in FIG. 7. In the crack growth evaluating simulation, the crack growth evaluation apparatus 1 performs a crack growth evaluating process on a crack occurring in the soldered portion 102 using a eutectic solder of SnPb which is a solder material of the soldered portion 102 as a continuum.

The soldered portion 102 in the analysis model shown in FIG. 8 is further enlarged to be equal to FIG. 15. That is, FIG. 15 is a further enlarged view of a part of the analysis model shown in FIG. 8. FIGS. 10 to 13 correspond to FIG. 15, and shows a result of crack growth evaluation according to the present invention on the analysis model.

FIG. 9 shows the temperature cycle applied to the soldered portion 102. In one cycle of the temperature cycle, the soldered portion 102 is held at 125° C. for 30 minutes after being held at −40° C. for 30 minutes. The actual period of one cycle is about 1.16 hours. The crack growth evaluation apparatus 1 performs a crack growth evaluating process using the temperature condition of the temperature cycle shown in FIG. 9 as the information about the load to be applied to the soldered portion 102.

FIGS. 10 to 13 show a result of a crack growth evaluating simulation. Actually, FIGS. 10 to 13 show the screen of a display unit displayed by the crack growth display unit 15. In FIGS. 10 to 13, the rightmost of the screen shows a bar colored depending on the number of a finite element to display the color indicating the size of the cumulative damage value D of the finite element of the soldered portion 102.

In the bar, the area with diagonal lines indicates that the cumulative damage value D is a value exceeding a predetermined threshold. In the soldered portion 102 shown in FIG. 10, the area with the same diagonal lines as the diagonal line area in the bar includes a finite element (finite element whose rigidity is close to 0) having a cumulative damage value D exceeding the predetermined threshold. Therefore, the diagonal line area in the soldered portion 102 is a portion in which a crack has occurred (grown).

FIGS. 10, 11, 12, and 13 show status of the growth of a crack of a finite element of the soldered portion 102 at a 200 cycle termination point, at a 500 cycle termination point, at a 700 cycle termination point, and at a 900 cycle termination point, respectively. With reference to FIGS. 10 to 13, it is clear that the crack portion expands (grows) with an increasing number of cycle count of a temperature cycle applied to the soldered portion 102.

Figure 14:
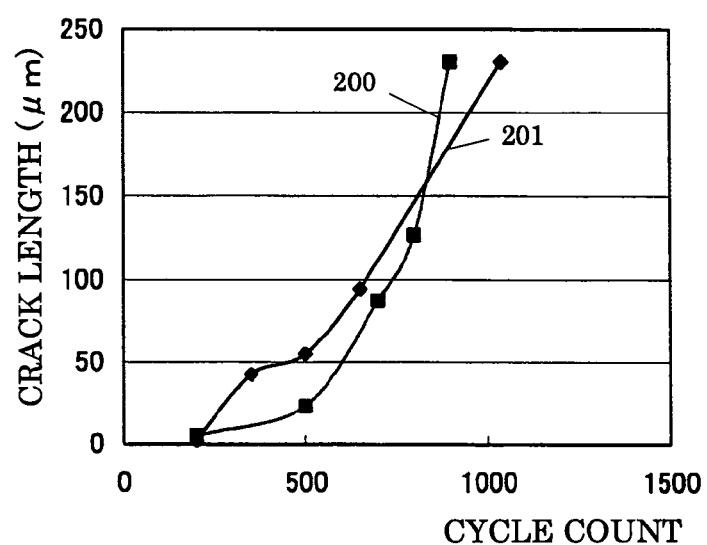
FIG. 14 shows the length of a crack occurring in a soldered portion for each cycle count.

FIG. 14 shows the length of a crack occurring in the soldered portion for each predetermined cycle count calculated by the crack growth evaluation apparatus in the crack growth evaluating simulation. The display unit 15 of the crack growth evaluation apparatus 1 calculates and displays the length of a crack occurring in the soldered portion 102 based on the area information about a crack growing portion shown in FIGS. 10 to 13. In FIG. 14, a curve 200 indicates the length calculated by the crack growth evaluation apparatus 1, and a curve 201 shows an actual value of the length of a crack. According to the crack growth evaluation apparatus 1 of the present invention, a simulation of the growth of a crack can be performed generally correctly.

As described above, the crack growth evaluation apparatus according to the present invention can display, for example, the growth of a crack up to the final fracture after the growth of the crack in the soldered portion with high accuracy. As a result, the present invention can estimates the complete fracture life of the soldered portion with high accuracy.

Additionally, the crack growth evaluation apparatus according to the present invention can display the growth of a crack occurring in the soldered portion and the growth direction of the crack for each predetermined load cycle. Therefore, the present invention can easily recognize a portion for which the reinforcement by a design change is required in a soldered portion. Furthermore, by applying the crack growth evaluation apparatus according to the present invention to the soldered portion after the design change, the influence of the design change of a soldered portion can be easily recognized.

What is claimed is:

1. A crack growth evaluation apparatus with a processor that evaluates growth of a crack occurring in a continuum, comprising:
    a model generation unit running on the processor and generating an analysis model used in analyzing a stress and a distortion occurring in the continuum by a finite-element method and obtained by dividing the continuum into a plurality of finite elements;
    an analysis unit running on the processor and analyzing by the finite-element method a stress and a distortion occurring by a load cyclically applied to the continuum in each of the plurality of finite elements of the continuum for each cycle of the load using the analysis model;
    an evaluation unit running on the processor and evaluating damage caused by the distortion occurring in the continuum for each of the plurality of finite elements of the continuum for each cycle of the load cyclically applied to the continuum using the analysis model based on a result of an analysis by the analysis unit;
    a display unit running on the processor and displaying growth of a crack occurring in the continuum using the analysis model based on a result of an evaluation of the damage by the evaluation unit; and
    a change unit running on the processor and changing rigidity of each of the plurality of finite elements of the continuum based on the result of the evaluation of the damage using the analysis model,
    wherein the analysis unit analyzes the stress and the distortion occurring by a load in a next cycle to a current cycle on each of the plurality of finite elements of the continuum whose rigidity has changed by the load of the current cycle of cycles of the load.

2. The crack growth evaluation apparatus according to claim 1,
    wherein the change unit changes the rigidity by changing each Young's modulus or yield stress of a plurality of finite elements of the continuum.

3. The crack growth evaluation apparatus according to claim 1,
    wherein the evaluation unit calculates a cumulative nonlinear distortion value on each of the plurality of finite elements of the continuum, calculates a nonlinear distortion amplitude value based on the cumulative nonlinear distortion value, calculates a damage value using a Manson-Coffin law based on the nonlinear distortion amplitude value, calculates a cumulative value of the damage value based on the damage value, and compares the cumulative value with a predetermined threshold, and
    wherein the change unit changes the rigidity of a finite element on each of the plurality of finite elements of the continuum based on result of a comparison by the evaluation unit.

4. The crack growth evaluation apparatus according to claim 3,
    wherein the evaluation unit calculates the nonlinear distortion amplitude value in the current cycle by subtracting a cumulative nonlinear distortion value in a cycle immediately before the current cycle from a cumulative nonlinear distortion value in the current cycle of the cycles of the load for each of the plurality of finite elements of the continuum.

5. The crack growth evaluation apparatus according to claim 3,
    wherein the evaluation unit obtains an average value of the cumulative nonlinear distortion value based on the cumulative nonlinear distortion value in a cycle of the load in a predetermined order and a count up to the cycle of the load in the predetermined order for each of the plurality of finite elements of the continuum, and calculates the nonlinear distortion amplitude value in the cycle of the load in the predetermined order based on the average value.

6. The crack growth evaluation apparatus according to claim 3,
    wherein the evaluation unit calculates a damage value obtained when a load equal to a load in the current cycle of the cycles of the load is applied to the continuum by a number of times of a predetermined value for each of the plurality of finite elements of the continuum by multiplying a damage value in the current cycle by the predetermined value.

7. The crack growth evaluation apparatus according to claim 3,
    wherein the evaluation unit calculates a change rate of the damage value for each of the plurality of finite elements of the continuum, and calculates the damage value obtained when applying a load equal to a load in the current cycle of the cycles of the load to the continuum a number of times of a predetermined value corresponding to the change rate by multiplying a damage value in the current cycle by the predetermined value.

8. The crack growth evaluation apparatus according to claim 7,
wherein the predetermined value corresponding to the change rate is stored in a storage unit in advance, and is determined based on correspondence information between a change rate of the damage value of each of the plurality of finite elements of the continuum and a predetermined value.

9. The crack growth evaluation apparatus according to claim 1,
wherein the display unit displays growth of a crack occurring in the continuum for one or more predetermined load cycles.

10. The crack growth evaluation apparatus according to claim 1,
wherein the display unit calculates and displays a length of a crack occurring in the continuum for one or more predetermined load cycles.

11. The crack growth evaluation apparatus according to claim 10,
wherein the display unit calculates a complete fracture life of the continuum based on information on the length of the crack and dimension of the continuum.

12. The crack growth evaluation apparatus according to claim 1,
wherein the continuum includes a soldered portion of an electronic component.

13. A crack growth evaluation method for evaluating growth of a crack occurring in a continuum comprising:
generating an analysis model used in analyzing a stress and a distortion occurring in the continuum by a finite-element method and obtained by dividing the continuum into a plurality of finite elements;
analyzing by the finite-element method a stress and a distortion occurring by a load cyclically applied to the continuum for each of the plurality of finite elements of the continuum in each cycle of the load using the analysis model;
evaluating damage caused by the distortion occurring in the continuum for each of the plurality of finite elements of the continuum for each cycle of the load cyclically applied to the continuum using the analysis model based on a result of the analysis; and
displaying the growth of a crack occurring in the continuum using the analysis model based on a result of the evaluation of the damage; and
changing rigidity of each of the plurality of finite elements of the continuum based on the result of the evaluation of the damage using the analysis model,
wherein the analyzing analyzes the stress and the distortion occurring by a load in a next cycle to a current cycle on each of the plurality of finite elements of the continuum whose rigidity has changed by the load of the current cycle of cycles of the load.

14. A non-transitory tangible recording medium recording a crack growth evaluation program for evaluating growth of a crack occurring in a continuum, the program causing a computer to execute:
generating an analysis model used in analyzing a stress and a distortion occurring in the continuum by a finite-element method and obtained by dividing the continuum into a plurality of finite elements;
analyzing by the finite-element method a stress and a distortion occurring by a load cyclically applied to the continuum in each of the plurality of finite elements of the continuum for each cycle of the load using the analysis model;
evaluating damage caused by the distortion occurring in the continuum for each of the plurality of finite elements of the continuum for each cycle of the load cyclically applied to the continuum using the analysis model based on a result of the analysis;
displaying the growth of a crack occurring in the continuum using the analysis model based on a result of the evaluation of the damage; and
changing rigidity of each of the plurality of finite elements of the continuum based on the result of the evaluation of the damage using the analysis model,
wherein the analyzing analyzes the stress and the distortion occurring by a load in a next cycle to a current cycle on each of the plurality of finite elements of the continuum whose rigidity has changed by the load of the current cycle of cycles of the load.

* * * * *